(12) United States Patent
Ramberg et al.

(10) Patent No.: US 12,714,494 B2
(45) Date of Patent: Aug. 25, 2026

(54) HANDHELD PULSED FIELD ABLATION GENERATOR

(71) Applicant: Medtronic, Inc., Minneapolis, MN (US)

(72) Inventors: Steven V. Ramberg, North Oaks, MN (US); Daniel S. Cheek, Plymouth, MN (US); Steven J. Fraasch, Maple Grove, MN (US); Brian Howard, Minneapolis, MN (US); John D. Norton, Saint Paul, MN (US); Nicolas Coulombe, Montreal (CA)

(73) Assignee: Medtronic, Inc., Minneapolis, MN (US)

( * ) Notice: Subject to any disclaimer, the term of this patent is extended or adjusted under 35 U.S.C. 154(b) by 1266 days.

(21) Appl. No.: 16/360,334

(22) Filed: Mar. 21, 2019

(65) Prior Publication Data

US 2019/0350647 A1 Nov. 21, 2019

Related U.S. Application Data

(60) Provisional application No. 62/674,405, filed on May 21, 2018.

(51) Int. Cl.
*A61B 18/14* (2006.01)
*A61B 18/12* (2006.01)
(Continued)

(52) U.S. Cl.
CPC ...... *A61B 18/1492* (2013.01); *A61B 18/1206* (2013.01); *A61M 5/14* (2013.01); (Continued)

(58) Field of Classification Search
CPC ...................... A61N 1/327; A61B 2018/00613
See application file for complete search history.

(56) References Cited

U.S. PATENT DOCUMENTS 9,597,143 B2 3/2017 Madan et al.
10,159,507 B2 * 12/2018 Craig ............. A61B 17/320092
(Continued)

FOREIGN PATENT DOCUMENTS

EP 2851017 A1 3/2015

OTHER PUBLICATIONS

International Search Report and Written Opinion dated Jun. 26, 2019, for corresponding International Application No. PCT/US2019/023331; International Filing Date: Mar. 21, 2019 consisting of 11-pages.

(Continued)

*Primary Examiner* — Linda C Dvorak
*Assistant Examiner* — Christine A Dedoulis
(74) *Attorney, Agent, or Firm* — Michael Best & Friedrich LLP

(57) ABSTRACT

A medical device may include an electrosurgical hand piece. The electrosurgical hand piece may have a housing with a proximal end, a distal end, and a chamber proximate the proximal end. The chamber may be configured to releasably retain and electrically couple with a power source. The electrosurgical hand piece may also include a treatment delivery element configured to releasably couple to the distal end of the housing. The treatment delivery element may be configured to communicate with the power source and deliver biphasic pulsed field ablation. The medical device may also include a charging element which may charge the power source using inductive charging or near-field (RF) wireless charging.

20 Claims, 5 Drawing Sheets

(51) Int. Cl.
*A61M 5/14* (2006.01)
*A61N 1/32* (2006.01)
*A61B 18/00* (2006.01)

(52) U.S. Cl.
CPC .... *A61N 1/327* (2013.01); *A61B 2018/00577* (2013.01); *A61B 2018/00613* (2013.01); *A61B 2018/1467* (2013.01); *A61B 2218/002* (2013.01); *A61M 2205/054* (2013.01)

(56) References Cited

U.S. PATENT DOCUMENTS

2008/0042861 A1* 2/2008 Dacquay ................ G01R 31/40 340/636.1
2010/0152725 A1* 6/2010 Pearson ............ A61B 18/1815 606/41
2011/0276113 A1 11/2011 Cybulski
2012/0004652 A1 1/2012 Moua et al.
2012/0059286 A1 3/2012 Hastings et al.
2012/0110810 A1* 5/2012 Houser ................ H02J 7/0044 29/271
2017/0189097 A1 7/2017 Viswanathan et al.
2018/0235509 A1* 8/2018 Doron ................. A61B 5/6852
2018/0303543 A1 10/2018 Stewart et al.

OTHER PUBLICATIONS

China National Intellectual Property Administration Notice of Second Office Action for Application No. 201980032440.6 dated Apr. 1, 2024 (16 pages including English translation).

China National Intellectual Property Administration Notice of First Office Action for Application No. 201980032440.6 dated Sep. 6, 2023 (14 pages including English translation).

European Patent Office Action for Application No. 19715672.2 dated Dec. 7, 2023 (4 pages).

China National Intellectual Property Administration Third Office Action for Application No. 201980032440.6 dated Jun. 24, 2024 (13 pages including English translation).

* cited by examiner

HANDHELD PULSED FIELD ABLATION GENERATOR

CROSS-REFERENCE TO RELATED APPLICATION

This application claims the benefit of U.S. Application Ser. No. 62/674,405, filed May 21, 2018.

FIELD

The present technology is generally related to a portable pulsed field ablation (PFA) system. In particular, the invention relates to a wireless handheld device and a system for delivering pulsed field ablation to tissue.

BACKGROUND

Ablation of tissue is a tool for the treatment of various medical conditions which include, but are not limited to, arrhythmias like atrial fibrillation, atrial flutter, and ventricular tachycardia as well as other electrophysiological abnormalities. Many medical devices configured to ablate tissue require cords or cables to directly connect to an external power source while the medical device is in use. However, when a corded connection is used during a medical procedure where tissue is being ablated, the user may have issues maneuvering as space can be significantly limited in the location where the procedure is taking place. Given size limitations of procedure rooms, surgical suites, and doctors' offices, it can be challenging to find an appropriate location for the components associated with a medical device used to ablate tissue. It can also be difficult for a user to use a corded medical device with various external units as the cords themselves can create hazards. The cord can make it difficult for a medical provider to freely move around with the medical device while treating a patient as the medical device is always connected with the cord and presents a tripping hazard. Additionally, if a user inadvertently disconnects the device during use, the potential exists to create an electrical hazard. Electric cords have the potential to fray or separate after several uses.

Furthermore, a cord that is connected to a power source can pose electrical risks for the patient. When there are cords connected to a power source, such as the energy that comes from a wall outlet, there is significant risk of leakage current should isolation barriers break down. Additional risks include power surges, brown outs and/or coupled noise, all which can pose significant risk and or injury to both physician and patient. Cords can become entangled as physicians articulate and rotate catheter handles, which at times can require disconnection and reconnection of cords. This exposes connectors to blood, saline, and other conductive fluids which can cause shorts across electrical paths.

In corded devices, there are typical restraints which can hinder the medical providers' ability to maneuver the device.

SUMMARY

The techniques of this disclosure generally relate to a method and system for a wireless medical device to deliver ablation energy to specific targeted tissue. Some embodiments advantageously provide a method and system for providing ablation energy to tissue while using a wireless power source. Other parts of the medical device which previously required a cord may now be wireless including, but not limited to, a controller, a power source, a receiver, as well as other components of the medical device which may make it safer and easier to use.

In one aspect, the present disclosure provides a medical system that includes a medical device, comprising: an electrosurgical hand piece including: a housing defining a proximal end, distal end, and a chamber proximate the proximal end, the chamber being configured to releasably retain and electrically couple with a power source; and a treatment delivery element configured to releasably couple to the distal end of the housing, the treatment delivery element being configured to communicate with the power source and deliver biphasic pulsed field ablation.

In one aspect, the present disclosure provides that the electrosurgical hand piece further includes a capacitor, the capacitor being configured to be in communication with the power source and the treatment delivery element.

In one aspect, the present disclosure provides that the capacitor further includes a user interface with a display configured to indicate when power is being drawn from the power source.

In one aspect, the present disclosure provides that the electrosurgical hand piece further includes an h-bridge, the h-bridge being configured to be in communication with the capacitor, the power source, and the treatment delivery element.

In one aspect, the present disclosure provides that the power source, capacitor, h-bridge, and the treatment element are all axially aligned.

In one aspect, the present disclosure provides that the treatment delivery device is a focal catheter.

In one aspect, the present disclosure provides that the electrosurgical hand piece further includes a fluid delivery tube configured to releasably couple with the housing.

In one aspect, the present disclosure provides that the power source is rechargeable.

In one aspect, the present disclosure provides that the power source is configured to be charged using inductive charging.

In one aspect, the present disclosure provides a medical system, comprising: an electrosurgical hand piece including: a housing defining a proximal end and a distal end, and a chamber proximate the proximal end, the chamber being configured to releasably retain and electrically couple with a power source; a capacitor in communication with the power source and distal to the chamber; an h-bridge in communication with the power source and the capacitor; and a treatment delivery element configured to releasably couple to the distal end of the housing, the treatment delivery element being configured to communicate with the power source, the capacitor, and the h-bridge, and deliver biphasic pulsed field ablation: and an inductive charging element configured to charge the power source when in proximity to the power source.

In one aspect, the present disclosure provides that the inductive charging plate is sterile.

In one aspect, the present disclosure provides that the electrosurgical hand piece is sterile.

In one aspect, the present disclosure provides that the treatment delivery element is a focal catheter.

In one aspect, the present disclosure provides that the focal catheter has a plurality of electrodes, the plurality of electrodes being axially aligned along the focal catheter.

In one aspect, the present disclosure provides that the capacitor further includes a user interface with a display that indicates the charge of the battery.

In one aspect, the present disclosure provides that the display that further includes a light-emitting diode.

In one aspect, the present disclosure provides that the chamber includes a hinged portion disposed proximate the proximal end.

In one aspect, the present disclosure provides that the electrosurgical hand piece further includes a fluid delivery tube configured to releasably couple with the housing.

In one aspect, the present disclosure provides that the electrosurgical hand piece further includes a wireless communication device in communication with a remote recording system configured to record electrical signals.

In one aspect, the present disclosure provides a medical system comprising: an electrosurgical hand piece including: a housing defining a proximal end and a distal end and a chamber proximate the proximal end, the chamber being configured to releasably retain and electrically couple with a power source; a wireless communication device disposed proximate the chamber; a capacitor in communication with the power source and the wireless communication device, the capacitor disposed distal to the wireless communication device; a user interface with a display disposed on the capacitor; an h-bridge in communication with the power source, the wireless communication device, and the capacitor and distal to the capacitor; and a treatment delivery element with a plurality of electrodes disposed axially along the treatment delivery element, the treatment delivery element being configured to communicate with the power source, the capacitor, the wireless communication device, and the h-bridge, and deliver biphasic pulsed field ablation: and an inductive charging element configured to charge the power source when in proximity to the power source.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
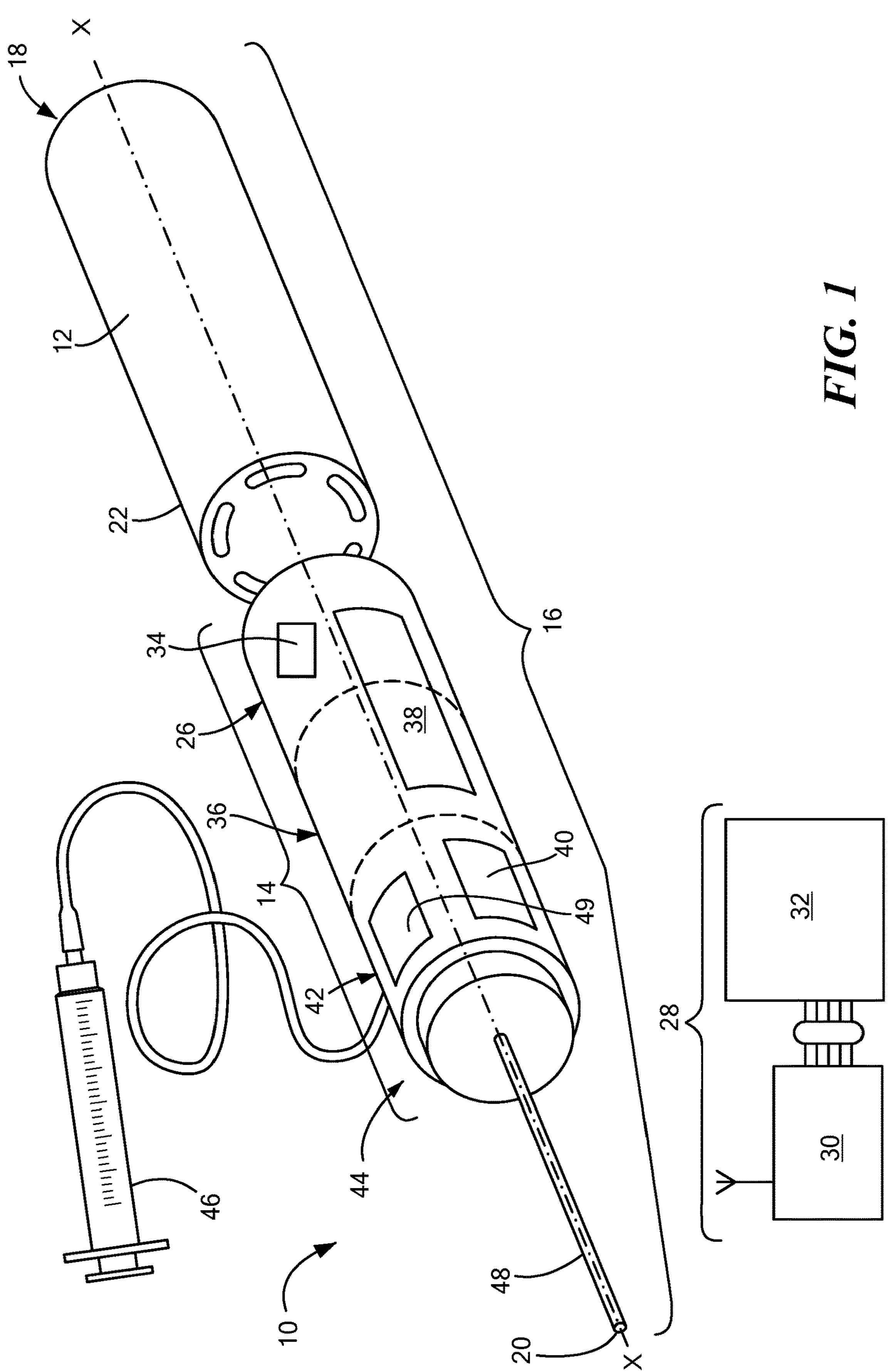
FIG. 1 is a front perspective view of an exemplary configuration of a medical device including an electrosurgical hand piece.

Before describing in detail exemplary embodiments that are in accordance with the disclosure, it is noted that the components have been represented where appropriate by conventional symbols in drawings, showing only those specific details that are pertinent to understanding the embodiments of the disclosure so as not to obscure the disclosure with details that will be readily apparent to those of ordinary skill in the art having the benefit of the descriptions herein.

As used herein, relational terms, such as “first” and “second,” “top” and “bottom,” and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms “a”, “an” and “the” are intended to include the plural forms as well, unless the context clearly indicates otherwise. It will be further understood that the terms “comprises,” “comprising,” “includes” and/or “including” when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, “in communication with” and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication. In addition, the term “in fluid communication with” may be used to describe a fluid pressure or flow connection between points, such as a fluid connection on the handle of a device that delivers fluid through a passage in the catheter to an electrode or distal site on the device.

The device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate figures not expressly indicated on other figures or embodiments, it is understood that the features and components of the system and devices disclosed herein are not necessarily exclusive of each other and may be included in a variety of different combinations or configurations without departing from the scope and spirit of the invention.

Referring now to the drawing figures in which like reference designators refer to like elements, an embodiment of a medical device is shown in FIG. 1, generally designated as “10.” The medical device 10 includes an integral power source 12 configured so the medical device 10 to be portable and untethered from traditional wall power, as discussed in more detail below. The medical device 10 includes an electrosurgical hand piece 14 configured to deliver bipolar pulsed field ablation to reversibly or irreversibly electroporate a target tissue region. The shape of the electrosurgical hand piece 14 may be customized for a particular user with a variety of different shapes and sizes and the configurations described herein are merely exemplary. In the configuration shown in FIG. 1, the electrosurgical hand piece 14 may include a housing 16 with a proximal end 18 and a distal end 20. As a non-limiting example, the proximal end 18 and the distal end 20 may be axially aligned along a longitudinal axis ("x") as shown in FIG. 1. Along the longitudinal x axis, the housing 16 may be configured to retain components from the medical device 10. A chamber 22 may be disposed proximate the proximal end 18 and may be configured to releasably retain and electrically couple with the power source 12. The chamber 22 may be hollow inside and shaped like a barrel, a channel, a rectangle, a circle, an oval, or any other shape that may be configured to retain and electrically couple with the power source 12. The power source 12 may be sealed within the chamber 22 or it may be releasably retained within the chamber 22 such that a user could remove and replace the power source 12 from the chamber 22. If the power source 12 is sealed within the chamber 22, the entire chamber 22 may be removable from the electrosurgical hand piece 14 such that another chamber 22 and power source 12 may be coupled with the electrosurgical hand piece 14.

The power source 12 may be rechargeable or non-rechargeable and in one embodiment may include a battery. As a non-limiting example, in FIG. 1 the power source 12 may be a single AA battery. Alternatively, more than one battery may be used as the power source 12. The different types of batteries may include, but are not limited to, a lithium-ion battery, an aluminum-ion battery, a flow battery, a lead-acid battery, a glass battery, a lithium air battery, a magnesium-ion battery, a molten salt battery, a nickel-cadmium battery, a nickel hydrogen battery, and an alkaline battery. If the power source 12 is rechargeable, it may be charged using either conductive charging or inductive charging. Having the power source 12 that is not directly connected to a wall socket electrically isolates the medical device 10 as well as the patient thereby reducing the risk of a power surge and minimizing any signal leakage where the signal is not being properly contained.

The power source 12 may be configured to provide enough energy to ablate tissue using a pulsed train of energy having a predetermined frequency. As a non-limiting example, the power source 12 in one embodiment may produce up to 1500 volts. Pulsed electroporation energy may be delivered to specific body tissue which can include, but is not limited to cardiac tissue, tissue within the ear, renal tissue, airway tissue, and organs or tissue within the cardiothoracic space. Electroporation may use high amplitude pulses to effectuate a physiological modification of the cells to which the energy is applied. These pulses may be short in order to allow the application of high voltage as well as a high current without a long duration of electrical current flow. Depending upon the specific characteristics of the electrical pulses, the electroporated cells may reach a reversible or irreversible state. A user may set the amount of energy that is to be delivered to the cells using the medical device 10 such that different cells may receive different amounts of energy in the electrical pulses or the same cells may receive different amounts of energy from each electrical pulse. The amount of energy to be delivered using the medical device 10 may also have the same amount of energy in each pulse. The power source 12 may be configured to provide numerous electrical pulses using the same power source 12.

A wireless communication device 26 may be disposed distal to the chamber 22. The wireless communication device 26 may be in communication with a remote recording system 28 and be electrically coupled with the power source 12. The wireless communication device 26 may be capable of sending and receiving information from the remote recording system 28. As a non-limiting example, the remote recording system 28 may have a remote electrocardiogram (EGM) box 30 which is in further communication with an electrophysiology (EP) reporting and recording system 32 which may be manufactured by, Cardiotek®, Siemens®, GE Pruka, and Bard Electrophysiology and may record information about the electrical activity in patient tissue.

A microelectromechanical system (MEMS) 34 may be incorporated with the wireless communication device 26 and may be electrically coupled with the power source 12. The MEMS 34 may receive power from the power source 12 associated with the medical device 10 or a separate power source may be electrically coupled with the MEMS 34 to provide energy for the MEMS 34. The MEMS 34 may be in communication with the remote EGM box 30 and the remote EP reporting and recording system 32 to receive and transmit information and/or instructions. The MEMS 34 may configure to monitor electrical signals received from target tissue and provide the device with specific instructions on how to treat the tissue based upon the electrical signals received from the target tissue. A microprocessor may also be incorporated into the MEMS 34 to execute logical and computation tasks with various integrated circuits or the microprocessor may be disposed at another location.

A capacitor 36 may be disposed distal to the wireless communication device 26. The capacitor 36 may be in communication with and electrically coupled to the power source 12 and the wireless communication device 26. The capacitor 36 may be a shaped in a variety of different shapes, including but not limited a cylinder. The capacitor 36 may also be integral to the power source 12. The capacitor 36 may be a single capacitor or a group of several capacitors of the same rating that are connected in series or parallel with each other to store electrical energy. The resulting capacitor 36 bank may be a high density capacitor 36 bank that is used to counteract or correct a power factor lag or phase shift in an alternating current (AC) power supply. Alternatively, the resulting capacitor 36 bank may be used in a direct current (DC) power supply to increase the ripple current capacity of the power supply or to increase the overall amount of energy stored. Various configurations of one capacitor 36 or multiple capacitors 36 may be used depending upon how and where the medical device 10 is being used.

A user interface 38 may be disposed anywhere on the electrosurgical hand piece 14. The user interface 38 may have a display 40 which may be configured to provide a variety of different types of information, including, but not limited to, various status messages. For example, the display 40 may indicate when power is being drawn from the power source 12 when the medical device 10 is in use. The display 40 may also indicate the charge level of the power source 12, when the medical device 10 is in use, when the power source 12 should be replaced and/or recharged, when there is a functional problem with the medical device 10, as well as other information about the medical device 10. The display 40 may include light-emitting diodes (LED) or another light source that illuminates the display 40 or provides a message to the user which is either in words, symbols, or sounds. As a non-limiting example, the LED may be multi-colored and provide a user with the power on/off status. Multiple different statuses may be displayed through the use of different color lights and the number of flashes. Messages may also appear on the display 40 to provide information to the user. In an alternative embodiment, the user interface 38 may also alert a user to relevant information aloud so that a user does not have to read the display 40 for information.

Continuing to refer to FIG. 1, an h-bridge 42 may be disposed on the housing 16 distal to the capacitor 36 as an electronic circuit that enables voltage to be applied across a load in an opposite direction. Accordingly, the h-bridge 42 may be configured to facilitate the direction of the electrical current to be controlled using certain switches when a treatment delivery element 44 is in use. The h-bridge 42 may be configured to be in communication with and electrically coupled with the capacitor 36, the power source 12, the wireless communication device 26, and the treatment delivery element 44 such that the different components work together when ablation energy is being delivered through the treatment delivery element 44. The h-bridge 42 may receive information from various components in the medical device 10 and based on the information received the electrical current can be controlled in different ways. In one embodiment, the h-bridge 42 may deliver high voltage energy and the circuit within the h-bridge 42 may be switched out after the delivery of the energy.

A fluid delivery tube 46 may in fluid communication with the housing 16 or anywhere in or along the electrosurgical hand piece 14. The fluid delivery tube 46 may be configured to releasably couple with the housing 16 or the electrosurgical hand piece 14, or, alternatively, may be permanently coupled with the housing 16 or the electrosurgical hand piece 14. The fluid delivery tube 46 may be used as an intravenous line or as a syringe. As a non-limiting example, the fluid delivery tube 46 may contain therapeutic agents. The intravenous line or syringe may provide gene therapy or irrigation of a particular area of tissue. The fluid delivery tube 46 may be in communication with the wireless communication device 26 or another component of the medical device 10 and configured to operate based upon certain information/instructions received from the wireless communication device 26 or another component of the medical device 10. Alternatively, the user of the medical device 10 may manually operate the fluid delivery tube 46. As a non-limiting example, once pulsed electroporation energy is delivered to a particular body part, the cell pores may remain open for a period of time. While the cell pores are open, various chemicals may be injected into the pores using the fluid delivery tube 46 or another tube or device connected to the fluid delivery tube 46 such as an IV tube which is connected to the central lumen of the treatment delivery element 44. For example, for a patient with cancer this may allow a cancer treating agent/chemical to be injected into the cell.

The treatment delivery element 44 may be disposed distal to the h-bridge 42 and be configured to releasably couple with the distal end 20 of the housing 16. The capacitor 36 may be integral to the power source 12 and the treatment delivery element 44 with sufficient charge capacity to drive up to 35 Joules of energy. In one configuration, as shown in FIG. 1, the power source 12, the chamber 22, the wireless communication device 26, the capacitor 36, the h-bridge 42, and the treatment delivery element 44 may be axially aligned along the longitudinal x-axis either nesting into one another or linearly aligned. The treatment delivery element 44 may be configured to be in communication with and electrically coupled with the power source 12, the wireless communication device 26, the capacitor 36, and the h-bridge 42. The releasable coupling of the treatment delivery element 44 with the h-bridge 42 may occur with various different mechanisms including a bayonet mount, a plug, a releasable locking mechanism, or any other releasable coupling mechanism such that the treatment delivery element 44 may be secured to the electrosurgical hand piece 14 as well as easily removed. This enables a user to have different options as to what treatment delivery element 44 is to be used depending upon the type of treatment being provided to the patient and what tissue is being treated with the medical device 10.

Biphasic pulsed field ablation may be delivered by the treatment delivery element 44 as well as monophasic pulses. The treatment delivery element 44 may be a linear catheter, a focal catheter, any type of monopolar treatment device, or any type of bipolar treatment device including those in U.S. patent application Ser. No. 15/495,537, the entirety of which is expressly incorporated by reference herein. The treatment delivery element 44 may be configured to communicate with and electrically coupled with the power source 12 so that ablation energy may be delivered through the treatment delivery element 44 to the patient. If the treatment delivery element 44 is a focal catheter, there may be a single electrode or a plurality of electrodes 48 on the focal catheter. In one configuration, the plurality of electrodes 48 may be axially aligned along the longitudinal x-axis on the focal catheter. In an alternative configuration, the plurality of electrodes 48 may be in any desired configuration depending upon the treatment that is being delivered to the patient and what type of tissue is being treated. The electrodes 48 may be at the distal end of the treatment delivery element 44 or anywhere along the treatment delivery element 44 and configured in a circle, square, rectangle, oval, an irregular shape or any other configuration to provide treatment to different tissues. The treatment delivery element 44 may be completely removable from the electrosurgical hand piece 14.

A field-programmable gate array ("FPGA") 49 may be disposed on the h-bridge 42. The FPGA 49 may be a semiconductor device that is based around a matrix of configurable logic blocks connected via programmable interconnects. The FPGA 49 may be programmed and reprogrammed to a desired application or functionality requirements after manufacturing. The FPGA 49 may be in communication with the electrodes 48 on the treatment delivery element 44 and configured to activate and deactivate one specific electrode or more than one electrode 48 depending upon how the FPGA 49 has been programmed. The FPGA 49 may be in communication with a processor, such as a user interface program processor or a microprocessor which transmits signals through the FPGA 49 to activate or deactivate certain electrodes 48.

Figure 2:
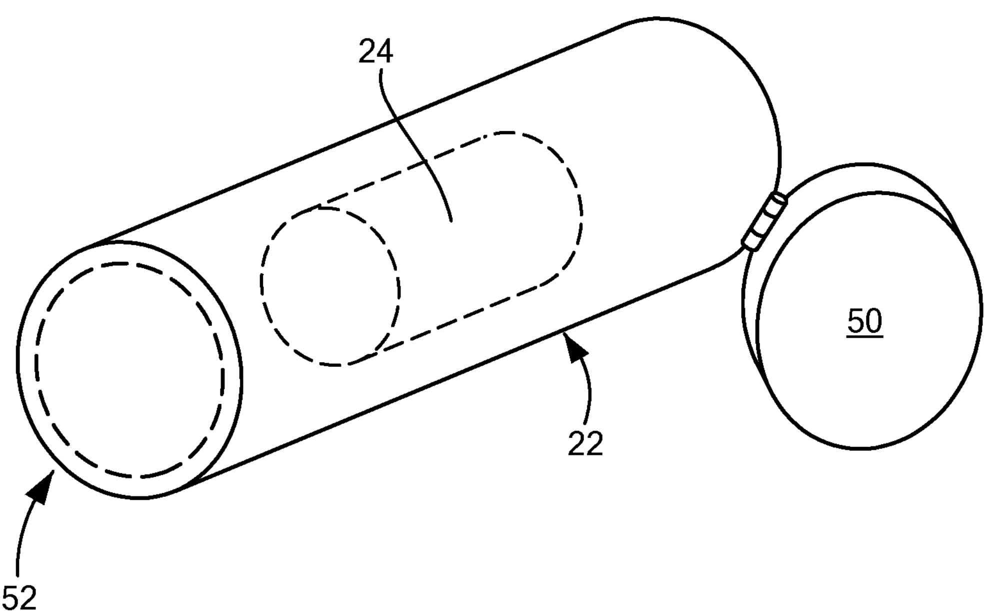
FIG. 2 is a front perspective view of a portion of the electrosurgical hand piece of FIG. 1 showing a power source retained within.

Now referring to FIG. 2, the chamber 22 may include the power source 12 which is releasably secured within the chamber 22. A proximal portion of the chamber 50 may be hinged so that the proximal portion of the chamber 50 may be opened and closed while the chamber 22 is still secured to the medical device 10. For example, a power source 12 such as a battery may be removed once the hinged portion of the chamber 50 is opened. In an alternative configuration, the proximal portion of the chamber 50 may be completely separable from the chamber 22. As a non-limiting example, the proximal portion of the chamber 50 may be a screw cap. The proximal portion of the chamber 50 may also be sealed to the chamber and not removable. A distal portion of the chamber 52 may also have a mechanism to secure the chamber 22 to the electrosurgical hand piece 14 and/or the housing 16. The chamber 22 may be releasably secured to the electrosurgical hand piece 14 and/or the housing 16 or it may be permanently affixed.

Figure 3:
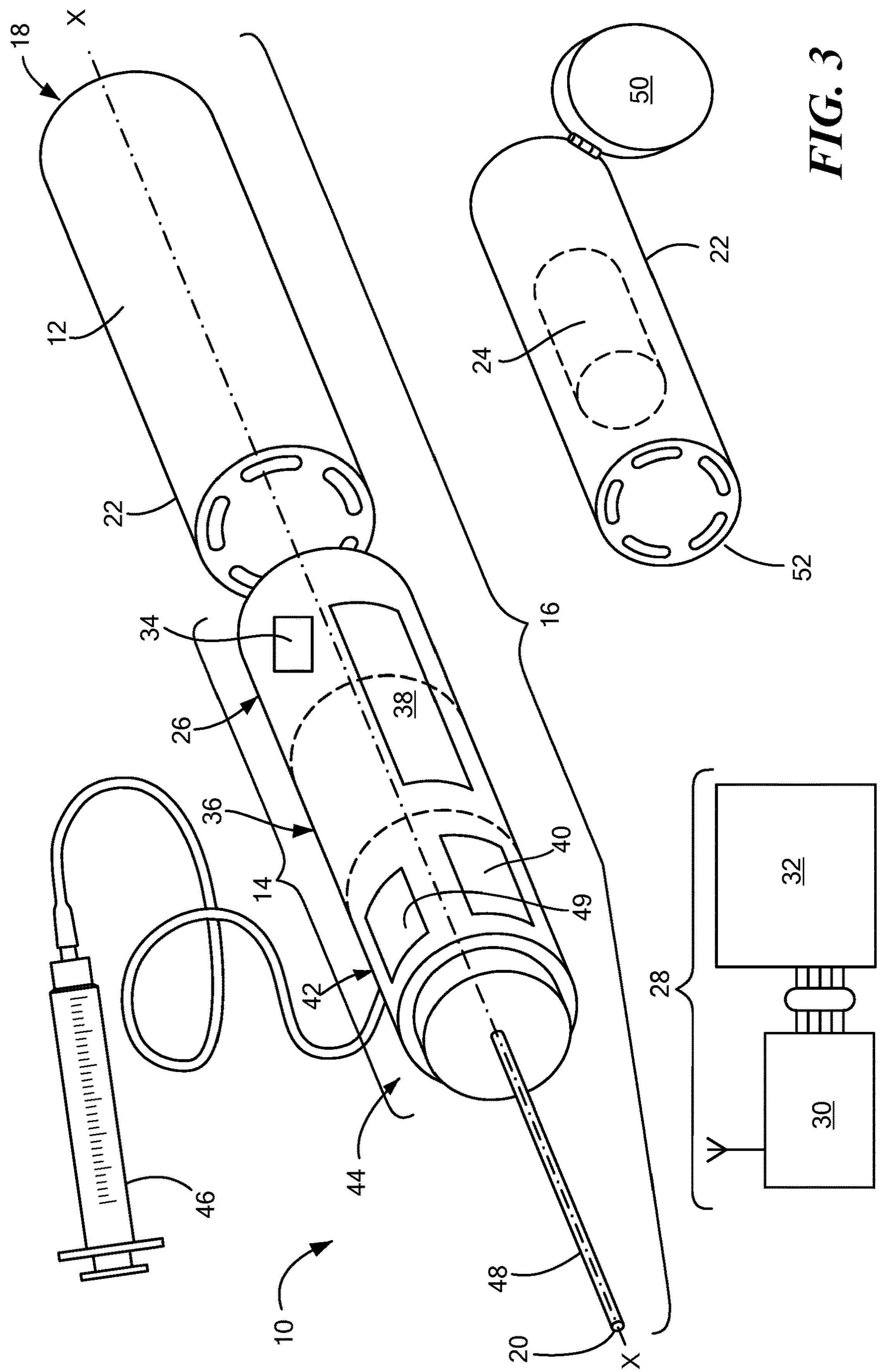
FIG. 3 is a front perspective view of the medical device shown in FIG. 1 with a different power source retained within.

Now referring to FIG. 3, there may be more than one chamber 22 as part of the medical device 10 such that the power source 12 within the chamber 22 may be separated from the medical device 10 and recharged. In this non-limiting example, the power source 12 may be a lithium ion battery which can be recharged and then used again. This may allow a chamber 22 to be connected to the electrosurgical hand piece 14. If the power source 12 within the chamber 22 becomes depleted and is no longer operable to provide the amount of energy needed during treatment with the medical device 10, another chamber 22 with the power source 12 may be used. The chamber 22 may be removed from the medical device 10, as a non-limiting example, with a twist-lock connection or any other removable connection such that the chamber 22 may be completely separated from the medical device 10. There may be as many additional chambers 22 with the power source 12 provided to the user such that the medical device 10 will always have an available power source 12. Either when the chamber 22 is connected to or separated from the medical device 10, the power source 12 inside the chamber 22 may be replaced. Multiple different types of power sources 12 may be used within the chamber 22 at one time or only one power source 12 may be used. This may allow the medical device 10 to be used for an extended period of time without having to recharge or replace the power source 12 within the chamber 22. As a non-limiting example, the power source 12 may deliver a pulse train in approximately 100 milliseconds.

Figure 4:
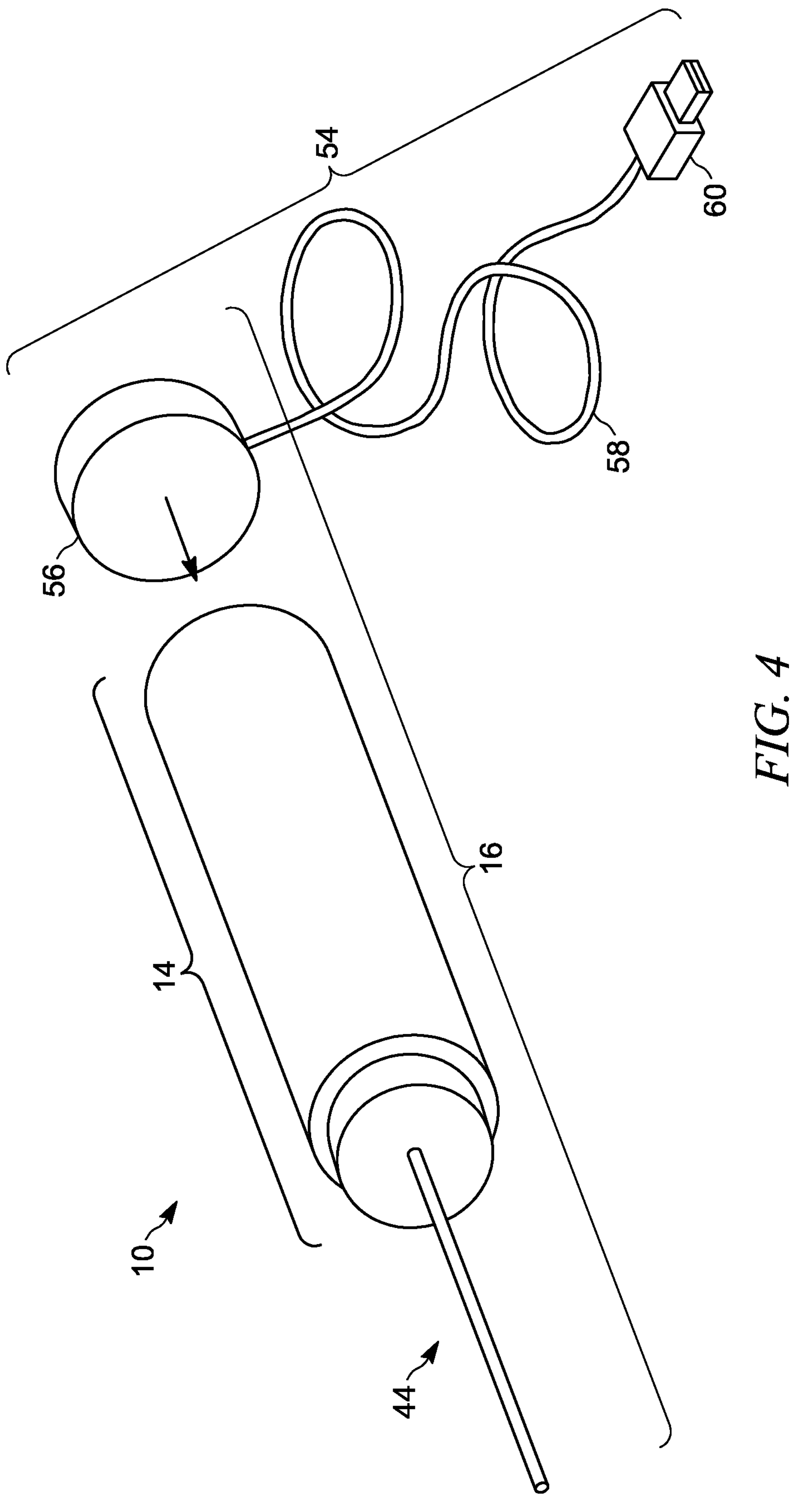
FIG. 4 is a side view of the medical device of FIG. 1 and an inductive charging plate.

Now referring to FIG. 4, the medical device 10 may also include a charging element 54. The charging element 54 may be an inductive charging element configured for near-field (RF) wireless charging. As a non-limiting example, the charging element 54 may include a charging plate 56, a cord 58 and a universal serial bus (USB) 60. The charging plate 56 may be configured to couple with the chamber 22, the power source 12, or another portion of the medical device 10 to recharge the power source 12. The charging plate 56 may be releasably secured to a portion of the medical device 10 or may be coupled with the medical device 10 so that the power source 12 may be recharged. In one configuration, the recharging of the power source 12 may occur in less than 10 seconds so that the power source 12 can be quickly reused during a medical procedure. Additionally, any other type of charging element that is compatible with the power source 12 used may be used to recharge the power source 12. The display 40 on the user interface 38 may indicate when the power source 12 needs to be charged, when the charging is occurring, and the level of charge of the power source 12. When the power source 12 is completely charged, the user interface 38 may have an audible indicator or a visual indicator to let a user know when the charging is completed. The charging element 54 may be sterilized so that charging can occur near the patient being treated or any portion of the charging element 54 may be sterilized such as the charging plate 56, the cord 58, and the USB 60. With the sterile environment, charging may occur while the medical device 10 is in use and in a sterile patient field or it may occur after the medical device has been removed from the sterile field.

Figure 5:
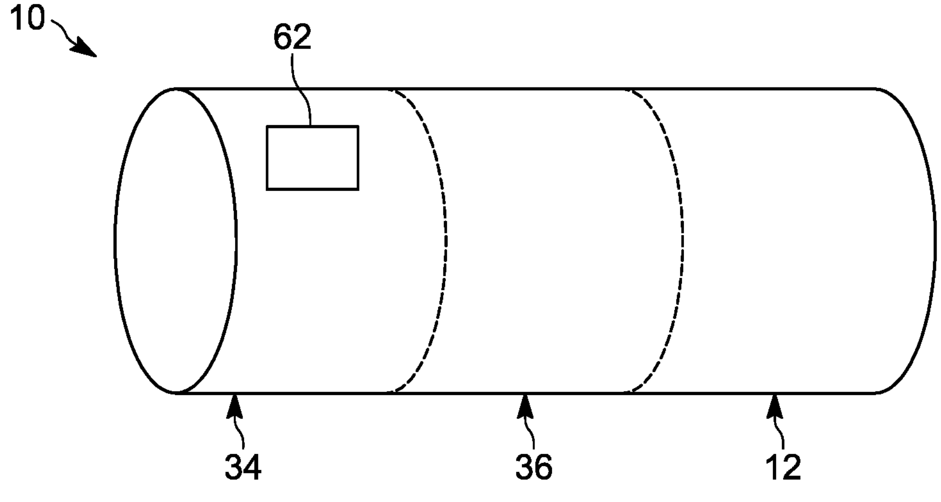
FIG. 5 is a medical system constructed in accordance with the principles of the present application.
Figure 5:
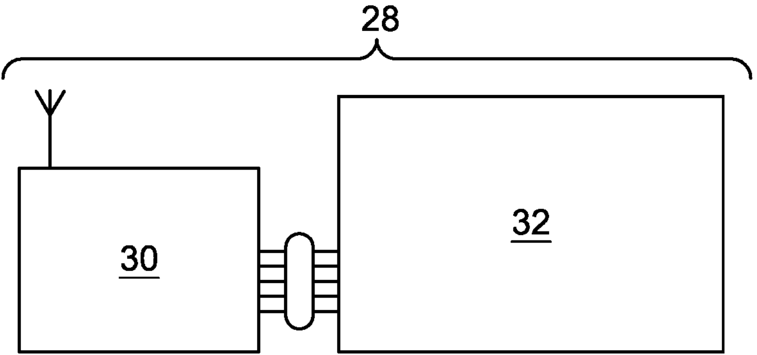

FIG. 5 is alternative configuration of the medical device 10 wherein the wireless communication device 26, the display 40, the h-bridge 42, the fluid delivery tube 46, and the FPGA 49 are not included. This alternative configuration includes at least a MEMS 34, a processor 62, a capacitor 36, a treatment delivery element 44, and a power source 12. The processor 62 may be a part of the MEMS 34 or it may be separate from the MEMS 34. While the medical provider is performing a procedure, the MEMS 34 and/or the processor 62 may obtain data from the procedure and store data from the procedure. While the procedure is ongoing, the data that is stored in the MEMS 34 and/or the processor 62 may be communicated to the remote recording system 28, including but not limited to the remote EP reporting and recording system 32 which may be uploaded, for example, onto a computer console. The remote recording system 28 may configured to receive cardiac electrical signals which can subsequently be displayed on a screen. As a non-liming example, the plurality of electrodes 48 may sense what is going on inside the body and communicate with the MEMS 34 such that a signal like an electromyography signal may be communicated with the remote recording system 28. The medical provider can obtain real-time data while the medical procedure is being performed on the patient. This can enable a provider to adjust the procedure depending upon the information being received in real time from the medical device 10 and how the patient is responding to the treatment.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:

an electrosurgical hand piece including:

a first housing having a proximal end and a distal end;

a second housing proximate the proximal end, wherein the second housing is configured to releasably retain and electrically couple with a battery, the battery configured to deliver up to 1500 volts, and wherein the second housing is removable from the first housing; and a treatment delivery element configured to releasably couple to the distal end of the first housing, the treatment delivery element being configured to communicate with the battery and deliver biphasic pulsed field ablation to electroporate target tissue using energy from the battery.

2. The medical device of claim 1, wherein the electrosurgical hand piece further includes a capacitor, the capacitor configured to be in communication with the battery and the treatment delivery element.

3. The medical device of claim 2, wherein the capacitor further includes a user interface with a display configured to indicate when power is being drawn from the battery.

4. The medical device of claim 3, wherein the electrosurgical hand piece further includes an h-bridge, the h-bridge configured to be in communication with the capacitor, the battery, and the treatment delivery element.

5. The medical device of claim 4, wherein the battery, capacitor, h-bridge, and the treatment delivery element are all axially aligned.

6. The medical device of claim 5, wherein the treatment delivery element is a focal catheter.

7. The medical device of claim 1, wherein the electrosurgical hand piece further includes a fluid delivery tube configured to releasably couple with the first housing.

8. The medical device of claim 1, wherein the battery is rechargeable.

9. The medical device of claim 8, wherein the battery is configured to be charged using inductive charging.

10. A medical system, comprising:

an electrosurgical hand piece including:

a first housing having a proximal end and a distal end;

a second housing proximate the proximal end, wherein the second housing is configured to releasably retain and electrically couple with a battery, the battery configured to deliver up to 1500 volts, and wherein the second housing is removable from the first housing;

a capacitor in communication with the battery and distal to the second housing;

an h-bridge in communication with the battery and the capacitor;

a treatment delivery element configured to releasably couple to the distal end of the first housing, the treatment delivery element being configured to communicate with the battery, the capacitor, and the h-bridge, and deliver biphasic pulsed field ablation to electroporate target tissue using energy from the battery via the capacitor and the h-bridge; and an inductive charging element configured to charge the battery when in proximity to the battery.

11. The medical system of claim 10, wherein the inductive charging element is sterile.

12. The medical system of claim 10, wherein the electrosurgical hand piece is sterile.

13. The medical system of claim 10, wherein the treatment delivery element is a focal catheter.

14. The medical system of claim 13, wherein the focal catheter has a plurality of electrodes, the plurality of electrodes being axially aligned along the focal catheter.

15. The medical system of claim 10, wherein the capacitor further includes a user interface with a display that indicates the charge of the battery.

16. The medical system of claim 15, wherein the display further includes a light-emitting diode.

17. The medical system of claim 10, wherein the second housing includes a hinged portion disposed at a proximal end of the second housing, and wherein the hinged portion opens and closes to receive and releasably retain the battery.

18. The medical system of claim 10, wherein the electrosurgical hand piece further includes a fluid delivery tube configured to releasably couple with the first housing.

19. The medical system of claim 10, wherein the electrosurgical hand piece further includes a wireless communication device in communication with a remote recording system configured to record electrical signals.

20. A medical system comprising:

an electrosurgical hand piece including:

a first housing having a proximal end and a distal end;

a second housing proximate the proximal end, wherein the second housing is configured to releasably retain and electrically couple with a battery, the battery configured to deliver up to 1500 volts, and wherein the second housing is removable from the first housing;

a wireless communication device disposed proximate the second housing;

a capacitor in communication with the battery and the wireless communication device, the capacitor disposed distal to the wireless communication device;

a user interface with a display disposed on the capacitor;

an h-bridge in communication with the battery, the wireless communication device, and the capacitor and distal to the capacitor;

a treatment delivery element with a plurality of electrodes disposed axially along the treatment delivery element, the treatment delivery element being configured to communicate with the battery, the capacitor, the wireless communication device, and the h-bridge, and deliver biphasic pulsed field ablation to electroporate target tissue using energy from the battery via the capacitor and the h-bridge; and an inductive charging element configured to charge the battery when in proximity to the battery.

* * * * *